(12) United States Patent
Karim

(10) Patent No.: US 9,883,891 B1
(45) Date of Patent: *Feb. 6, 2018

(54) SPINAL FIXATION METHOD AND APPARATUS

(71) Applicant: Neurosurj Research and Development, LLC, Farmingdale, NY (US)

(72) Inventor: Syed Aftab Karim, Armonk, NY (US)

(73) Assignee: Versapine, LLC, Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,052

(22) Filed: Jun. 2, 2016

Related U.S. Application Data

(63) Continuation of application No. 15/017,121, filed on Feb. 5, 2016, now Pat. No. 9,561,055, which is a continuation-in-part of application No. 13/406,205, filed on Feb. 27, 2012, now Pat. No. 9,254,149.

(60) Provisional application No. 61/587,986, filed on Jan. 18, 2012.

(51) Int. Cl.
*A61B 17/70* (2006.01)
*A61B 17/68* (2006.01)

(52) U.S. Cl.
CPC ........ *A61B 17/683* (2013.01); *A61B 17/7002* (2013.01); *A61B 17/7007* (2013.01); *A61B 17/7055* (2013.01)

(58) Field of Classification Search
CPC .............. A61B 17/683; A61B 17/7007; A61B 17/7055
USPC ........ 411/380–383, 388–389, 396–398, 412, 411/542
See application file for complete search history.

(56) References Cited

U.S. PATENT DOCUMENTS

| | | | | |
|---|---|---|---|---|
| 930,810 | A | * | 8/1909 | Smith ..................... F16B 35/00 403/186 |
| 1,000,046 | A | * | 8/1911 | Stafford .................. F22B 7/16 403/186 |
| 1,742,201 | A | * | 1/1930 | Drissner ............... F16B 35/048 29/509 |
| 3,584,667 | A | * | 6/1971 | Reiland ................. B25B 13/065 411/402 |
| 3,741,205 | A | | 6/1973 | Markolf et al. |
| 3,900,025 | A | | 8/1975 | Barnes, Jr. |
| 4,790,303 | A | | 12/1988 | Steffee |
| 4,950,270 | A | | 8/1990 | Bowman et al. |
| 4,961,740 | A | | 10/1990 | Ray et al. |

(Continued)

OTHER PUBLICATIONS

Mummaneni, Praveen V., et al. "Posterior cervical fixation using a new polyaxial screw and rod system: technique and surgical results." Neurosurgical Focus 12.1 (2002): 1-5.

(Continued)

*Primary Examiner* — Ellen C Hammond
(74) *Attorney, Agent, or Firm* — Jones Walker LLP

(57) ABSTRACT

A spinal stabilization system having a pedicle screw which includes (i) a shaft with external threads and a head segment on one end of the shaft; (ii) a first drive socket positioned in the head segment; (iii) a second drive socket on a shaft end opposite the first drive socket; and (iv) wherein the shaft end opposite the first drive socket has a lesser diameter than the shaft end at the head segment. The system further includes an intervertebral stabilization structure having an elongated body with rotating ring segments attached to each end of the elongated body.

14 Claims, 16 Drawing Sheets

(56) References Cited

U.S. PATENT DOCUMENTS

| | | | |
|---|---|---|---|
| 5,030,052 A * | 7/1991 | Anderson | F16B 35/00 411/383 |
| 5,074,894 A | 12/1991 | Nelson | |
| 5,098,434 A | 3/1992 | Serbousek | |
| 5,169,400 A | 12/1992 | Muhling et al. | |
| 5,180,381 A | 1/1993 | Aust et al. | |
| 5,304,178 A | 4/1994 | Stahurski | |
| 5,324,290 A | 6/1994 | Zdeblick et al. | |
| 5,354,299 A * | 10/1994 | Coleman | A61B 17/1615 606/916 |
| 5,364,399 A | 11/1994 | Lowery et al. | |
| 5,443,509 A | 8/1995 | Boucher et al. | |
| 5,507,745 A | 4/1996 | Logroscino et al. | |
| 5,549,431 A | 8/1996 | Royle | |
| 5,549,612 A | 8/1996 | Yapp et al. | |
| 5,562,735 A | 10/1996 | Margulies | |
| 5,620,444 A | 4/1997 | Assaker | |
| 5,645,547 A | 7/1997 | Coleman | |
| 5,647,710 A * | 7/1997 | Cushman | F16B 35/00 411/389 |
| 5,688,273 A | 11/1997 | Errico | |
| 5,755,796 A | 5/1998 | Ibo et al. | |
| 5,904,683 A | 5/1999 | Pohndorf et al. | |
| 5,961,266 A * | 10/1999 | Tseng | F16B 37/12 411/289 |
| 5,994,720 A | 11/1999 | Snyman | |
| 6,086,590 A | 7/2000 | Margulies et al. | |
| 6,190,350 B1 | 2/2001 | Davis et al. | |
| 6,325,802 B1 | 12/2001 | Frigg | |
| 6,368,319 B1 | 4/2002 | Schaefer | |
| 6,423,065 B2 | 7/2002 | Ferree | |
| 6,613,051 B1 | 9/2003 | Luk et al. | |
| 6,764,507 B2 | 7/2004 | Shanley et al. | |
| 6,981,974 B2 * | 1/2006 | Berger | A61B 17/82 411/397 |
| 7,335,201 B2 | 2/2008 | Doubler et al. | |
| 7,588,402 B2 * | 9/2009 | Chuang | F16B 25/0021 411/383 |
| 7,892,260 B2 | 2/2011 | Mahoney et al. | |
| 7,942,910 B2 | 5/2011 | Doubler et al. | |
| 8,333,791 B2 | 12/2012 | Carls et al. | |
| 8,905,697 B2 * | 12/2014 | Gong | E04D 3/3606 411/371.1 |
| 9,254,149 B2 | 2/2016 | Karim | |
| 9,259,246 B2 * | 2/2016 | Brennan | A61F 2/4455 |
| 2002/0087161 A1 | 7/2002 | Randall et al. | |
| 2002/0099377 A1 | 7/2002 | Zucherman et al. | |
| 2002/0120272 A1 | 8/2002 | Yuan et al. | |
| 2003/0065329 A1 | 4/2003 | Vaughan | |
| 2003/0181914 A1 | 9/2003 | Johnson et al. | |
| 2004/0147929 A1 * | 7/2004 | Biedermann | A61B 17/7001 606/266 |
| 2004/0220573 A1 | 11/2004 | McDevitt et al. | |
| 2005/0228501 A1 | 10/2005 | Miller et al. | |
| 2006/0104742 A1 * | 5/2006 | Fleming | F16B 5/0275 411/389 |
| 2006/0122599 A1 | 6/2006 | Drewry et al. | |
| 2006/0200132 A1 | 9/2006 | Chao et al. | |
| 2006/0293660 A1 | 12/2006 | Lewis | |
| 2008/0058818 A1 | 3/2008 | Schwab | |
| 2008/0086131 A1 | 4/2008 | Daly et al. | |
| 2008/0125779 A1 | 5/2008 | Ferree | |
| 2008/0177322 A1 | 7/2008 | Davis et al. | |
| 2008/0247840 A1 * | 10/2008 | Davies | F16B 35/06 411/107 |
| 2009/0175701 A1 * | 7/2009 | Wu | F16B 35/044 411/383 |
| 2010/0249845 A1 | 9/2010 | Meunier | |
| 2010/0280554 A1 | 11/2010 | Vaidya | |
| 2010/0298881 A1 | 11/2010 | Lim et al. | |
| 2011/0046682 A1 | 2/2011 | Stephan et al. | |
| 2011/0071576 A1 * | 3/2011 | Hadi | A61B 17/683 606/301 |
| 2011/0112581 A1 | 5/2011 | Clement | |
| 2011/0137356 A1 | 6/2011 | Kollmer | |
| 2011/0218573 A1 | 9/2011 | Ferree | |
| 2011/0245875 A1 | 10/2011 | Karim | |
| 2011/0270314 A1 | 11/2011 | Mueller et al. | |
| 2016/0157897 A1 | 6/2016 | Vaidya | |
| 2016/0252125 A1 * | 9/2016 | Lares | B21J 5/08 411/402 |

OTHER PUBLICATIONS

"Surgical or Non-Surgical Treatments," www.zimmerspine.eu, downloaded Dec. 16, 2009, 10 pages.

Ullrich Jr., Dr. Peter F. "Pedicle Screws for Spine Fusion," Spine-Health, 2007, 4 pages.

Karim, A., Mukherjee, D., Ankem, M., Gonzalez-Cruz, J., Smith, D., & Nanda, A. (2006). Augmentation of anterior lumbar interbody fusion with anterior pedicle screw fixation: demonstration of novel constructs and evaluation of biomechanical stability in cadaveric specimens. Neurosurgery, 58(3), 522-527.

* cited by examiner

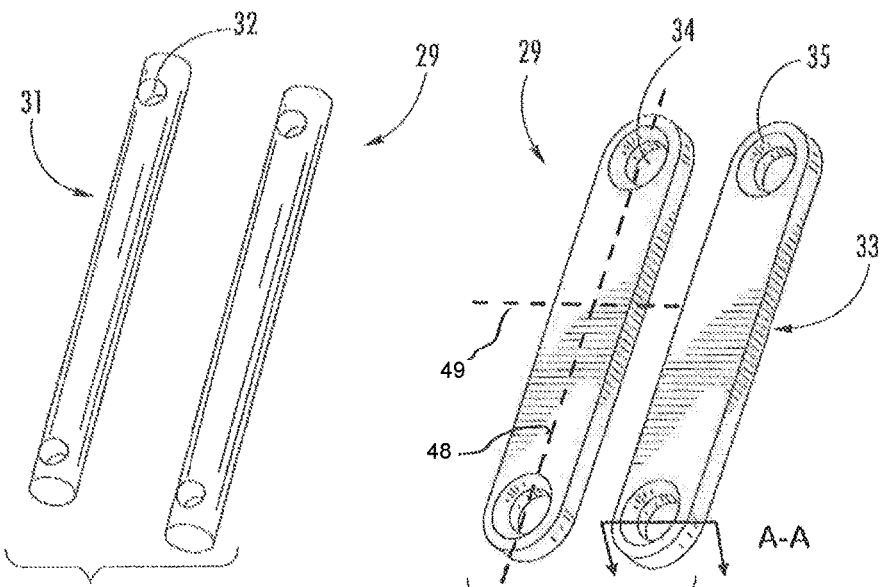
FIG. 5
FIG. 6a
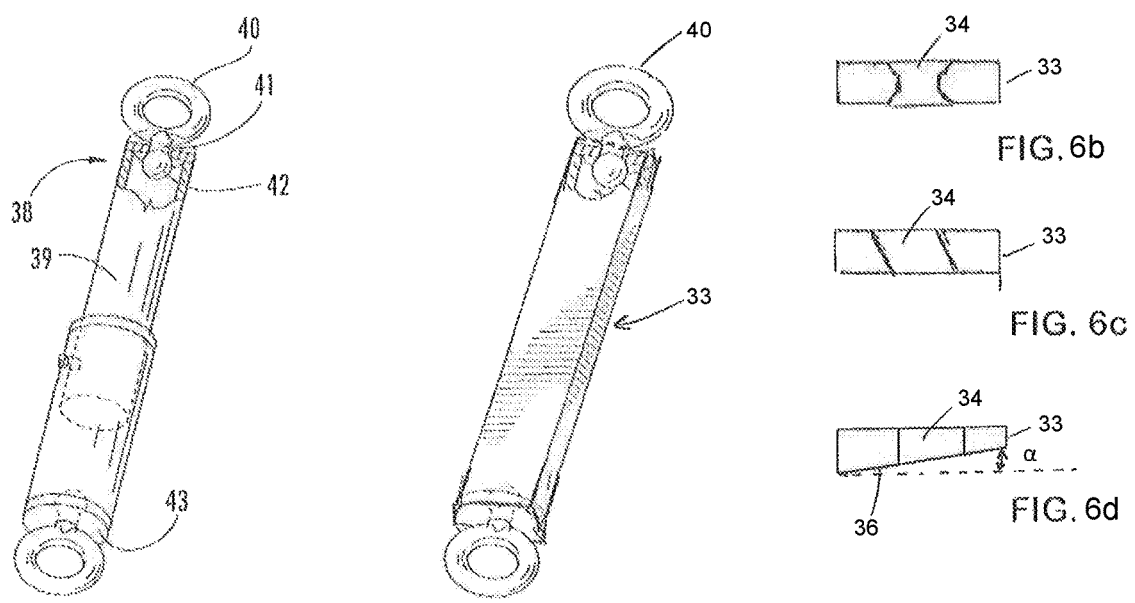
FIG. 7a
FIG. 7b
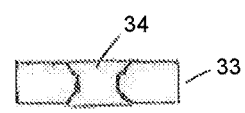
FIG. 6b
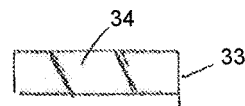
FIG. 6c
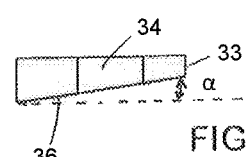
FIG. 6d

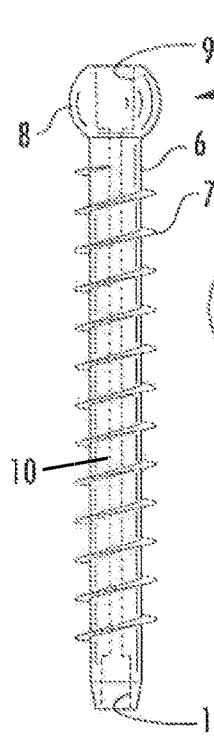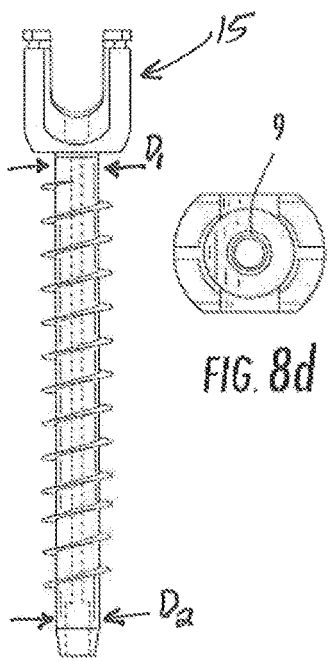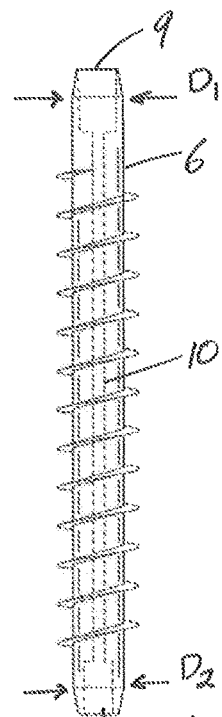
FIG. 8a  FIG. 8c  FIG. 8b  FIG. 8d  FIG. 8e
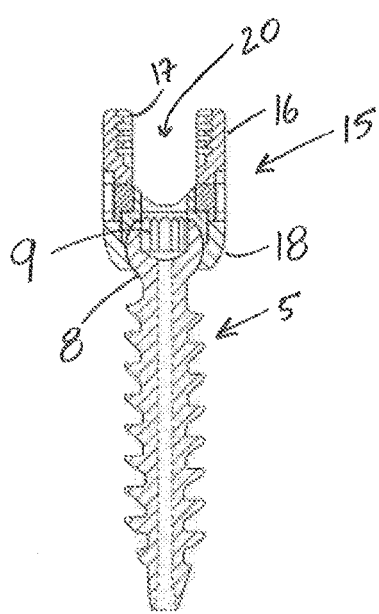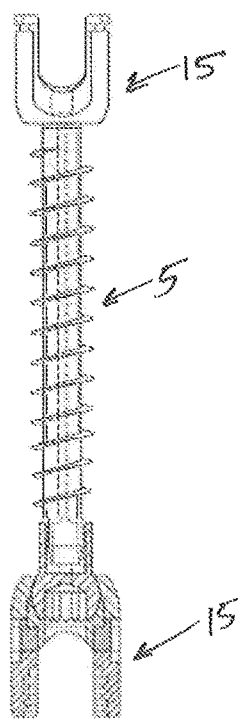
FIG. 8f  FIG. 8k

SPINAL FIXATION METHOD AND APPARATUS

CROSS REFERENCE TO RELATED APPLICATIONS

This application is a continuation of U.S. Nonprovisional application Ser. No. 15/017,121, filed Feb. 5, 2016, which application is a continuation-in-part of U.S. Nonprovisional application Ser. No. 13/406,205 filed Feb. 27, 2012, which claims the benefit under 35 USC 119(e) of U.S. Provisional Application Ser. No. 61/587,986, filed Jan. 18, 2012, all of which are incorporated by reference herein in their entirety.

FIELD OF INVENTION

The present invention relates to methods and devices for stabilizing the human spine.

BACKGROUND OF INVENTION

Various techniques for spinal stabilization or fusion are known in the art. Such techniques often utilize surgical implants which mechanically immobilize areas of the spine and may include eventual incorporation of grafting material. One technique for spinal fixation includes immobilization of the spine by the use of rods that run generally parallel to the spine. In practicing this technique, the posterior surface of the spine is exposed, and bone screws are first fastened to the pedicles of the appropriate vertebrae or to the sacrum, acting as anchor points for the rods. The bone screws are generally placed two per vertebrae, one at each pedicle on either side of the spinous process. Fasteners join the spine rods to the screws. Some techniques employ anterior fixation devices (i.e., devices position in the anterior side of the vertebrae with screws going into the bodies of the respective vertebrae), in alternative to or in combination with, the posterior devices described above.

BRIEF DESCRIPTION OF THE DRAWINGS

FIG. 5 illustrates one embodiment of an intervertebral stabilization structure.

FIG. 6a illustrates another embodiment of an interverbral stabilization structure.

FIG. 6b illustrates a cross-sections for the FIG. 6a embodiment.

FIG. 6c illustrates an alternative cross-sections for the FIG. 6a embodiment.

FIG. 6d illustrates an alternative cross-sections for the FIG. 6a embodiment.

FIG. 7a illustrates a further embodiment of an intervertebral stabilization structure.

FIG. 7b illustrates a modification of the FIG. 7a embodiment.

FIG. 8a illustrates one embodiment of a pedicle screw of the present invention.

FIG. 8b illustrates another embodiment of a pedicle screw of the present invention.

FIG. 8c illustrates a top view of the pedicle screw seen in FIG. 8a.

FIG. 8d illustrates a top view of the pedicle screw seen in FIG. 8b.

FIG. 8e illustrates another embodiment of a pedicle screw.

FIG. 8f illustrates a pedicle screw with a polyaxial connector assembly.

FIG. 8k illustrates an alternate pedicle screw with two polyaxial connectors.

DETAILED DESCRIPTION OF SELECTED EMBODIMENTS

Figure 1:
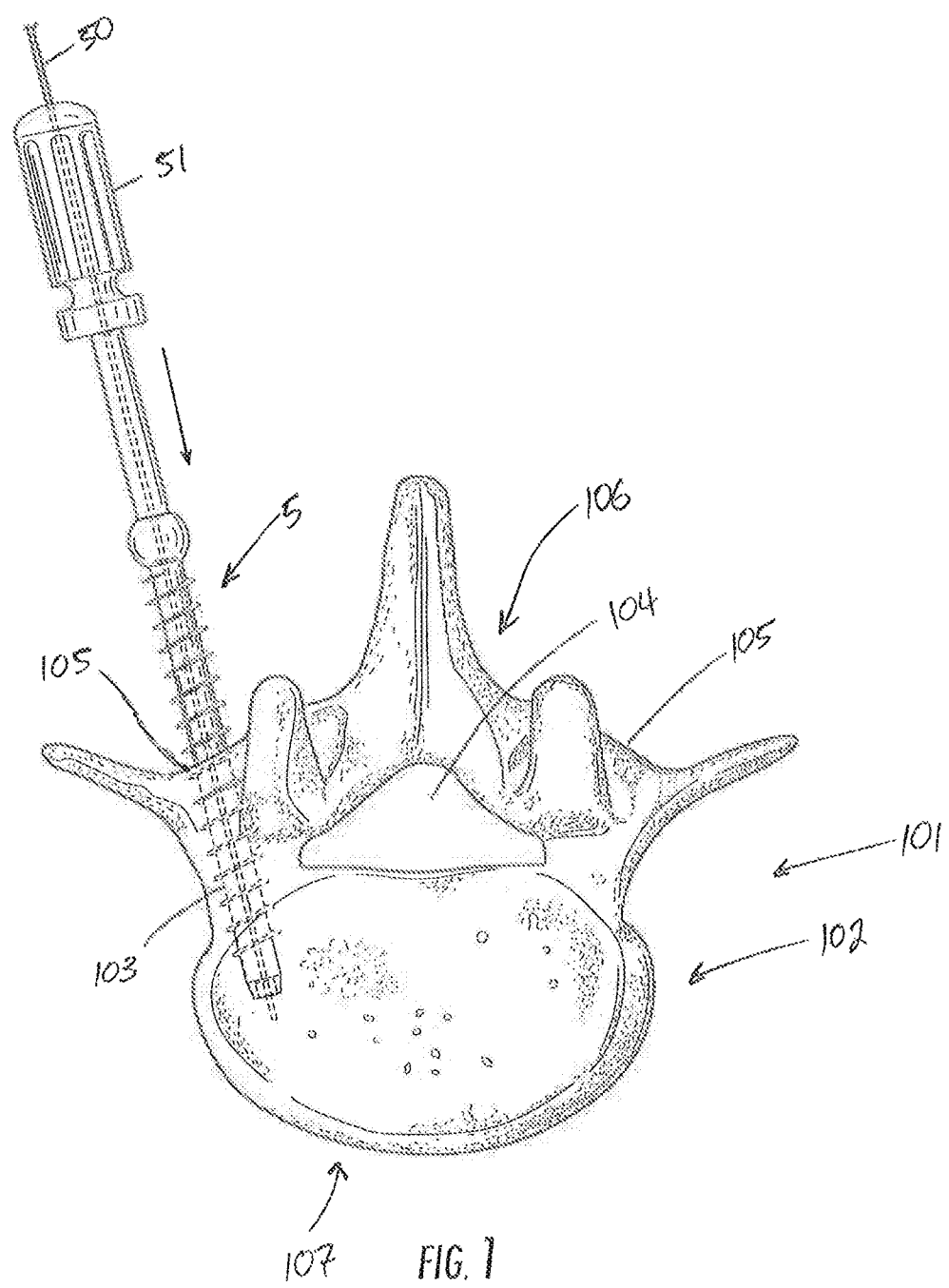
FIG. 1 illustrates an initial step in one method of the present invention.

One embodiment of the present invention is a method for spine stabilization, the steps of which can be generally understood by viewing FIGS. 1-4, 9, and 10. FIG. 1 is a cross-sectional illustration of a vertebra 101. While the figures are of lumbar vertebrae, the methods and structures described herein can be applied to vertebrae in other areas of the spine and the sacrum. FIG. 1 identifies the vertebral body 102, the pedicle 103, the foramen 104, the posterior side or surface (lamina) 106 of the vertebra (including pedicle entry point 105), and the anterior side or surface 107 of the vertebra.

In an initial step of the illustrated method embodiment, the patient is placed in the prone position (i.e., with posterior side of the vertebra facing upwards) as suggested by FIG. 1. Thereafter, the posterior pedical entry point is accessed by a conventional surgical technique, two nonlimiting examples being an open incision technique or a minimally invasive technique such as endoscopic surgery. FIG. 1 suggests where a screw 5 is advanced into the pedicle entry point 105 of a first vertebra and partially into the vertebral body 102, but without exiting the anterior surface 107 of the vertebral body.

It can be seen that FIG. 1 also illustrates a guide wire 50 extending through the screw 5 and the screw driving tool 51 and into the vertebral body 102. Although not explicitly shown, it will be understood that a conventional technique may be used to place the guide wire into the vertebra prior to attempting to insert the screw 5. In one example, the guide wire has a sharpened tip and is rotated with another tool so the guide wire bores along the path desired for the screw 5 to ultimately follow. An intra-operative imaging technique such as intra-operative x-ray, intra-operative CT, or other specific devices (e.g., an O-arm® imaging system such as produced by Medtronic, Inc. of Minneapolis, Minn.) may be used to allow the surgeon to advance the guide wire 50 along the desired path. After guide wire 50 is in place, various tools (e.g., drills, screw drivers, and screws) having center passages can be slid along guide wire 50 as suggested in FIG. 1. In the embodiment of FIG. 1, a ratcheting hand drill with a center passage could be employed to form a drill bore along the length of bone tissue into which guide wire 50 extends. Typically guide wire 50 need only extend into the bone far enough to establish the initial trajectory (e.g., 10-15 mm in one example) and the screw is advanced beyond the length of guide wire extending in the bone tissue. As one alternative to drilling with the guide wire itself, the surgeon may use a device such as a "gear shift" to form an initial bore in the bone tissue about 10-15 mm deep along the desired trajectory and insert a guide wire through a central passage in the gear shift and into the bore. The gear shift is then slid off the guide wire while retaining the guide wire in the bore. A screw with a central passage is slid over the guide wire and directed into the bore. A screw driver with a central bore is then used to advance the screw to the desired depth in the bone tissue. Although FIG. 1 and the above examples describe the use of a guide wire 50, the present surgical method may likewise be utilized with other surgical techniques not employing guide wires.

The screw 5 seen in FIG. 1 is illustrated in greater detail in FIGS. 8a to 8d. Screw 5 generally includes the shaft 6 having a series of external threads 7 positioned thereon. The embodiment of FIG. 8a has a spherical head 8 with a first drive socket 9 positioned within the spherical head. While the drive socket 9 in FIGS. 8a and 8d is a polygonal aperture (e.g., square, hexagonal, etc.), the drive socket could take on any shape (e.g., a conventional "straight cut" or "cross-cut" screw driver socket) and could be either a female or male surface for engaging a drive tool and transferring torque from the drive tool to the screw shaft. Screw 5 further includes a second drive socket 11 on the end of shaft 6 opposite the first drive socket 9. Again, second drive socket may be any shape or configuration which allows transfer of torque from a drive tool to the screw shaft. Second drive socket 11 may be the same shape as first drive socket 9 or more be of a different configuration. The embodiment of FIG. 8a includes a central passage or cannulation 10 traveling through shaft 6 from first drive socket 9 to second drive socket 11. However, the invention in not limited to screws with a central passage and alternate embodiment could include screws with a partial passage or a solid shaft, provided the shaft has ends accommodating the first and second drive sockets.

In certain embodiments of the invention, screw 5 will be what is generally known in the surgical art as a "pedicle" screw. For example, these embodiments of screw 5 will have approximate lengths of between about 20 and about 70 mm for more typical situations and lengths as short as 10 mm and as long as 100 mm in less typical situations (although the described embodiments are intended to cover any sub-range of lengths between 10 mm and 120 mm, e.g., 30 mm to 50 mm). The diameters of such screws will typically range from about 3.5 to about 7.5 mm or any sub-range of diameters between these dimensions. The smaller size range of screws would be more typical for pediatric patients and the larger size range more typical for large adults. In particular, a screw less than 3.5 mm in diameter could be employed in certain pediatric cases. While the figures illustrate a screw having pedicle-screw-like dimensions, other embodiments may employ screws which may not normally be considered pedicle screws. Nor do such screws need to be threaded along their entire length, but could have threads only along an end section in order to accommodate a mating threaded fastener.

In certain embodiments of screw 5, the shaft end opposite the first drive socket has a lesser outer diameter than the shaft end at the enlarged head segment. For example, in FIG. 8b, the shaft end at second drive head 11 has a diameter $D_2$ which is approximately 80% of the diameter $D_1$ of the shaft end engaging head segment 8, but may alternatively be 70%, 60%, 50% or possibly less of the diameter of the shaft end at the head segment.

Not all embodiments of screw 5 have an enlarged head portion such as spherical head 8. For example, FIG. 8e shows an embodiment where both the first drive socket 9 and the second drive socket 11 are formed internally to shaft 6 (with cannulation 10 running between the drive sockets). In FIG. 8e, the diameters of shaft 6 at the two ends ($D_1$ and $D_2$) are substantially equal. However, FIG. 8h illustrates an alternative embodiment where $D_1$ at the first end of shaft 6 is larger than $D_2$ at the second end of shaft 6. While shaft 6 is shown in FIG. 8h as having a substantially continuous taper between the two ends, other embodiments could have a stepwise or other noncontinuous transition between the two ends.

Figure 8G:
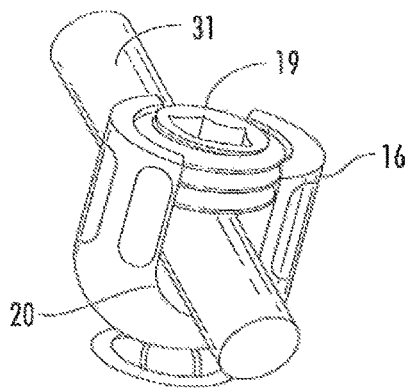
FIG. 8g illustrates a cap screw securing a rod to the polyaxial connector assembly.
Figure 8H:
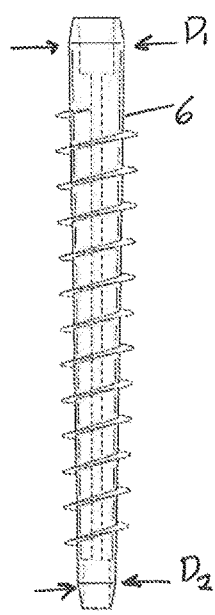
FIG. 8h illustrates a further embodiment of a pedicle screw.

One particular embodiment of screw 5 is suggested in FIGS. 8f and 8g. As best seen in FIG. 8f, this screw 5 will include the polyaxial connector assembly 15. Polyaxial connector assembly 15 will normally include a upper cup section 16 having opposing U-shaped crenellations 20 and internal threads 17. A lower cup connector 18 will grip the spherical head 8 allowing polyaxial connector assembly to rotate in all directions. As suggested by FIG. 8g, a cap screw 19 will engage internal threads 17 in order to securely grip a rod 31 or other stabilization device within the crenellations 20. Polyaxial connector assemblies are well known in the art, for example see U.S. Pat. No. 7,942,909 which is incorporated by reference herein in its entirety. FIG. 8f illustrates this embodiment of screw 5 having cannulation 10 and second drive socket 11. However, other embodiments of this screw 5 need not include the cannulation 10 and second drive socket 11.

Figure 8I:
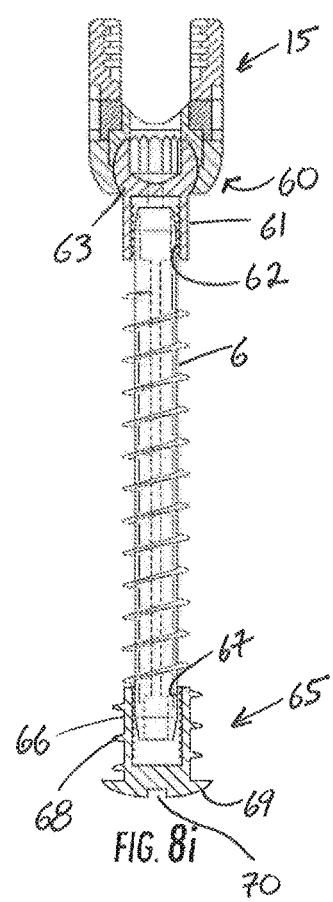
FIG. 8i illustrates a pedicle screw with a polyaxial connector and a cap member.

A further variation is suggested in FIG. 8i, where polyaxial connector assembly 15 is assembled onto shaft 6 by way of ball connector 60. Ball connector 60 includes spherical head portion 63 formed on shank 61. The internal threads 62 along shank 61 will engage threads on the first end of shaft 6. In a similar manner, the second end of shaft 6 may have a cap piece 65 threaded thereon. Cap piece 65 will also include a shank 66 having internal threads 67 for engaging that end of shaft 6. Cap piece 65 will have a comparatively flat (or slightly rounded) head portion to minimize any potential abrasion to arteries or organs. The embodiment of FIG. 8i also shows shank 66 with external threads 68, which are courser than internal threads 67 and configured to engage bone tissue. The cap pieces 65 may be considered anterior connectors configured for attaching the anterior stabilization bar to the pedicle screws.

Figure 8J:
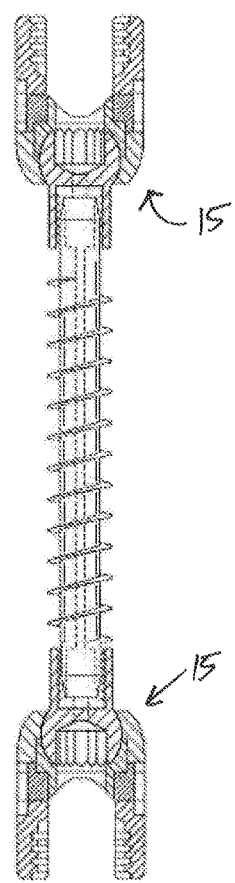
FIG. 8j illustrates a pedicle screw with two polyaxial connectors.

As further variations, FIG. 8k illustrates a pedicle screw 5 which has positioned on one end a polyaxial connector 15 such as seen in FIG. 8f, i.e., the head 8 is integrally formed on the shaft. However, the second end of pedicle screw 5 in FIG. 8k has a detachable polyaxial connector, i.e., the head is positioned on the shaft by threaded ball connector 60 such as seen in FIG. 8i. FIG. 8j illustrates a pedicle screw where threaded ball connectors 60 are positioned on each end of the screw shaft.

As described above, FIG. 1 suggests the screw 5 is advanced into the pedicle entry surface of a first vertebra and partially into the vertebral body 102, but without exiting the anterior surface 107 of the vertebral body. One reason for not advancing screw 5 beyond the anterior surface 107 is to avoid the danger of damaging blood vessels positioned adjacent to anterior surface 107; for example, the iliac artery or aorta resting adjacent to the anterior surface of the L3-L5 vertebrae.

Figure 2:
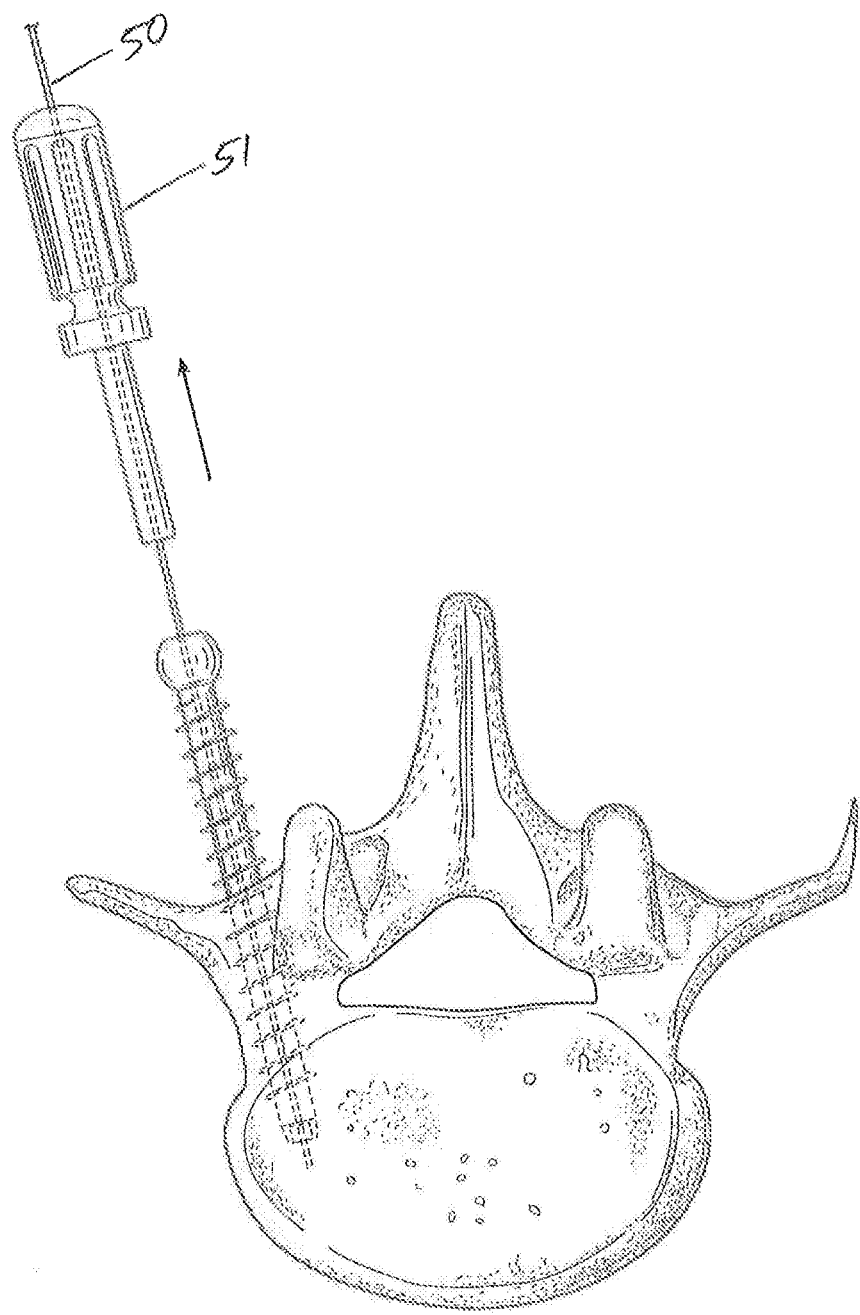
FIG. 2 illustrates a step subsequent to that shown in FIG. 1.
Figure 3:
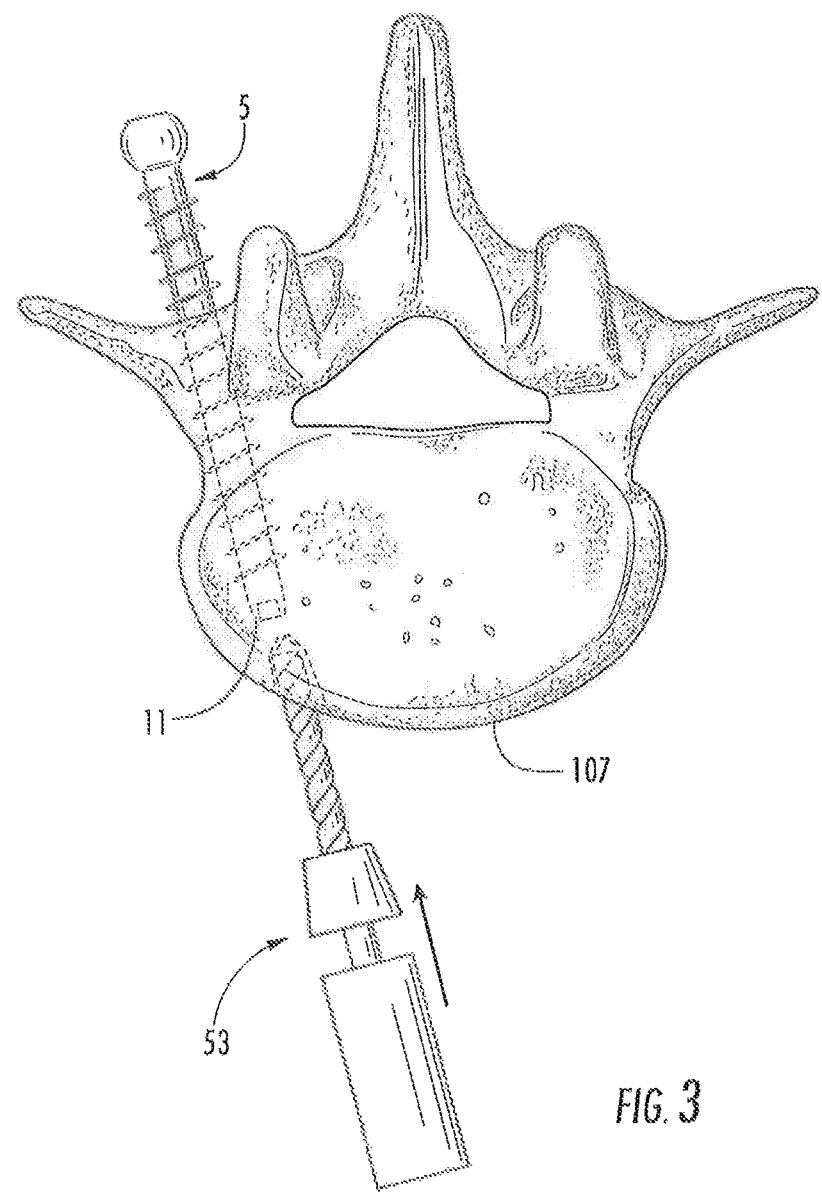
FIG. 3 illustrates a step subsequent to that shown in FIG. 2.

Next, FIG. 2 suggests how the drive tool 51 and guide wire 50 are removed, leaving screw 5 inside of vertebral body 102 but not exiting anterior surface 107. Thereafter, in one preferred embodiment of the method, the patient is then rotated to the supine position. The anterior surface 107 of the vertebral body 102 is then access through open incision technique or a minimally invasive technique as described above. After repositioning any vessels adjacent to the anterior surface section of interest, FIG. 3 suggests how the drill 53 will be used to drill through the anterior surface 107 and into the vertebral body 102 along an axis which will intersect the second drive socket 11 on screw 5. Many different techniques may be used to guide the direction of the drill into the anterior surface 107; for example, a neuronavigation system such as the Medtronic Stealth or Striker system, AP and lateral x-rays using the O-arm system described above, or the surgeon using his or her judgment to drill pilot holes where the tip of the screw is expected to be encountered. Once the drill has exposed the second drive socket 11, FIG. 4 suggests how drive tool 51 will be used to engage second drive socket 11 and advance screw 5 forward such that its end extends out of the anterior surface 107.

Although not explicitly shown in FIGS. 1-4, it will be understood that the same process for positioning screw 5 through the pedicle and anterior surface 107 will generally be performed bilaterally (i.e., on both the left and right sides of the vertebra) and at two or more levels (i.e., different vertebrae along the spine).

As described in more detail below, FIGS. 9 and 10 suggest how intervertebral stabilization structures (ISS) 29 will be connected to the screws 5 in order to complete the spinal stabilization procedure. The type of ISS 29 employed could vary widely depending on the procedure and FIGS. 5 to 7 are merely three illustrative examples of alternative ISS s. FIG. 5 shows solid cylindrical rods 31 having connecting apertures 32. FIG. 6a illustrates elongated plates 33 having connecting apertures 34 with beveled surfaces 35 allowing a screw head to seat more uniformly and form a lower overall profile. Rods 31 and plates 33 are examples of stabilization structures formed of a unitary body. FIG. 6a suggests how the rods 31 and plates 33 have a long axis 48 and a short axis 49. FIG. 6b illustrates a cross-section (section A-A in FIG. 6) of the aperture 34 and beveled surfaces 35 seen in FIG. 6a. As one alternative, FIG. 6c illustrates how the aperture 34 could be formed at an angle through the plate 33. As explained below in more detail with reference to FIG. 14, this angled aperture would better align with the trajectory of screw 5 in many spinal fixation procedures. As a further alternative, FIG. 6d suggests how the cross-section of plate 33 could itself be angled. In FIG. 6d, the surface 36 is sloped while aperture 34 is perpendicular to the opposite surface of plate 33. In the FIG. 6d embodiment, the angle formed by the sloped surface 36 as compared to the horizontal or short axis 49 (i.e., angle α in FIG. 6d) may be between about 5° and 45° (or any sub-range there between, e.g., about 15° and 35°). Thus, when surface 36 is positioned against the vertebra (e.g., in the orientation suggested by FIG. 14), the aperture 34 will have an angled orientation relative to the posterior-anterior axis through the spine (illustrated by the line PA in FIG. 4). FIG. 7 represents a third type of ISS comprising an elongated body 38 with rotating ring segments 40 attached to each end of the body. In this embodiment, the elongated body 38 is formed by two hollow cylinders 39a and 39b. Cylinder 39b is of a larger diameter and cylinder 39a is of a smaller diameter capable of sliding within cylinder 39b in a telescoping manner. A set screw 45 may be used to fix the relative positions of cylinders 39a and 39b, thereby allowing the length of this ISS to be adjusted to meet the requirements of the individual patient. A rotating ring segment 40 is shown as attached to a shaft 41 which is retained in hollow cylinder 39 by the enlarged end section 42 being larger than the aperture in end cap 43 through which shaft 41 extends. This arrangement allows the ring segment 40 to rotate in order to accommodate variations in screw trajectory and vertebra shape. However, elongated body 38 is not limited to the configuration seen in FIG. 7 and in other embodiments, elongated body 38 need not be telescoping, hollow, or cylindrical. In another embodiment not explicitly shown, shaft 41 could be threaded and engage threads formed in end cap 43, thereby allowing the distance between the two ring segments 40 to be adjusted in a manner similar to a conventional "turnbuckle" device. Structures such as seen in FIG. 7 may be referred to as "polyaxial stabilization structures" in the sense that they allow a rotative connection to the screws 5. Nor is the particular ISS in anyway limited to those shown in the figures, but could include virtually any existing of future developed ISS.

It will be understood that each of polyaxial connector assembly 15, the connecting apertures 32 in FIG. 5, the connecting aperture 34 in FIG. 6a and the swiveling ring segments 40 may be considered alternative "screw connectors" as used herein since they form the structure connecting the pedicle screw to the ISS. Likewise, the elongated bodies seen in FIGS. 5, 6a, and 7 may be considered different embodiments of "stabilization bars."

Figure 9:
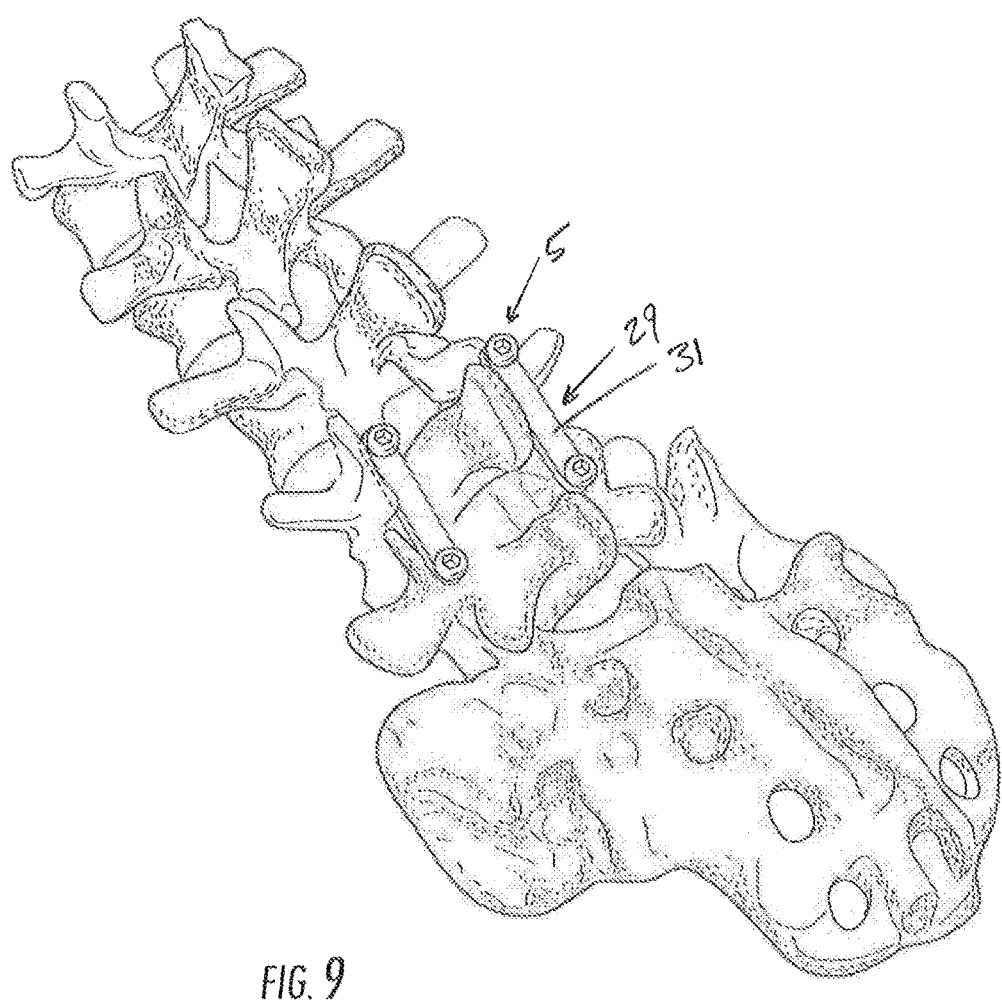
FIG. 9 illustrates one embodiment of intervertebral stabilization structures positioned along the posterior surface of the spine.
Figure 10:
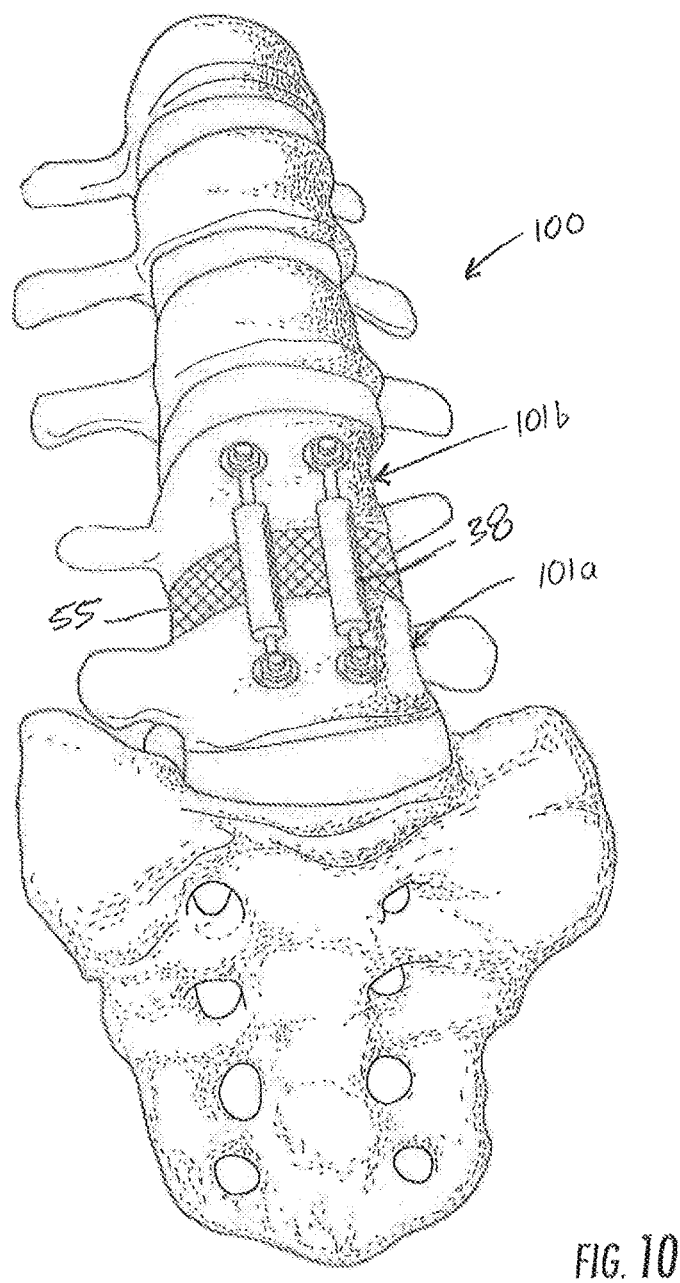
FIG. 10 illustrates another embodiment of intervertebral stabilization structures positioned along the anterior surface of the spine.

Viewing FIG. 9, this nonlimiting example suggest how the ISSs 29 on the posterior side of the spine are rods 31 which have the screws 5 extending through the rod aperture 32. FIG. 9 illustrates two ISSs 29 arranged in an ipsilateral manner (i.e., one ISS on each side of the posterior surface of the spine). Although FIG. 9 shows the ISSs 29 connected to adjacent vertebrae, it will be understood that the ISSs could also be connected to nonadjacent vertebrae (i.e., the connection skipping one or more vertebrae). Naturally this is merely one manner of connecting the ISSs to the screws and any number of connections mechanism could be employed, e.g., a polyaxial connector assembly with the rods 31 held in crenellations 20 by cap screws 19 as seen in FIG. 8f. Viewing the anterior side of the spine as shown in FIG. 10, this variation employs the ISSs having the ring segments 40 and shows the ends of screws 5 extending through ring segments 40 to the extent need to fix threaded nut-fasteners on the ends of screws 5. While FIGS. 9 and 10 show the ISSs fixed to adjacent vertebrae, other method embodiments could skip one or more levels between vertebrae to which the ISSs are attached, or have the ISSs attached to three or more vertebrae.

Figure 4:
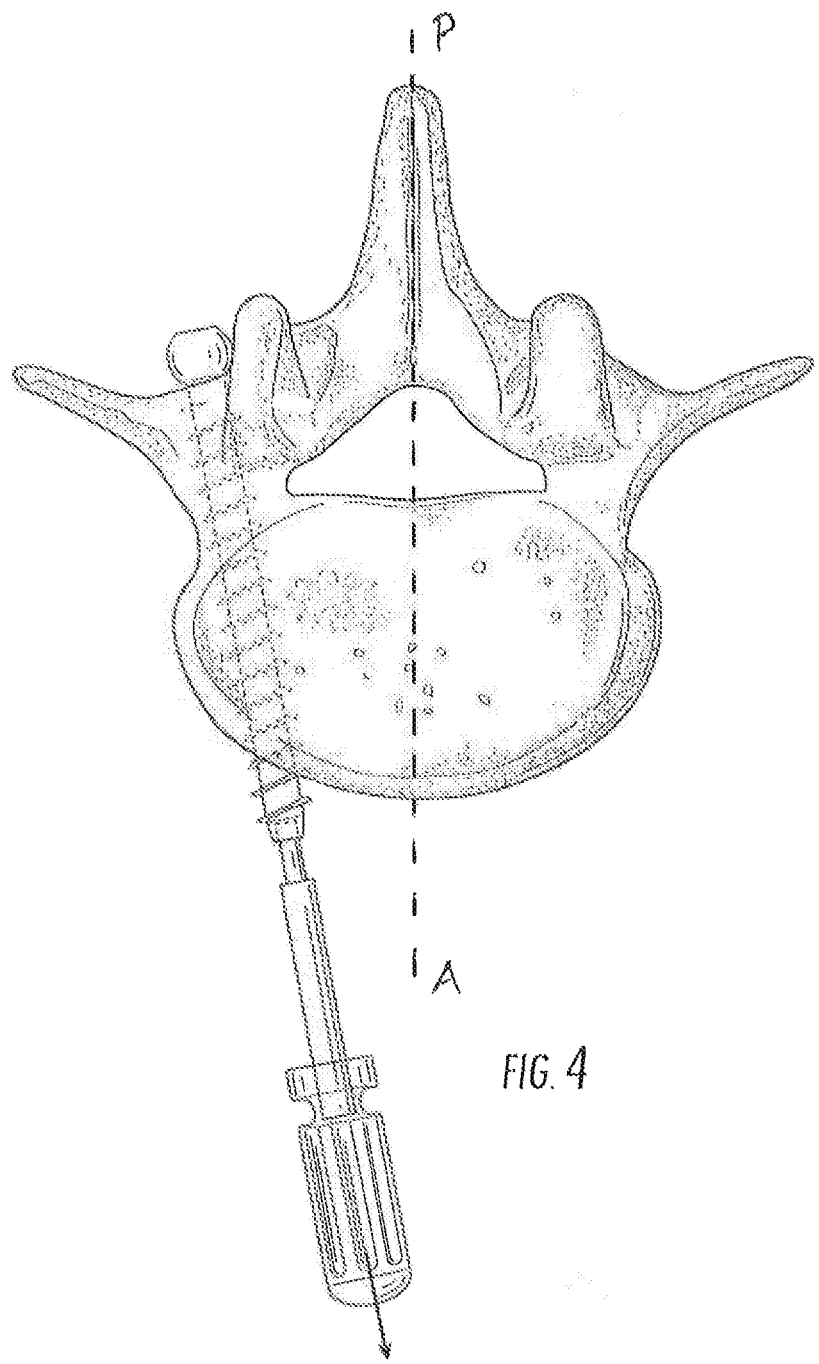
FIG. 4 illustrates a step subsequent to that shown in FIG. 3.
Figure 13:
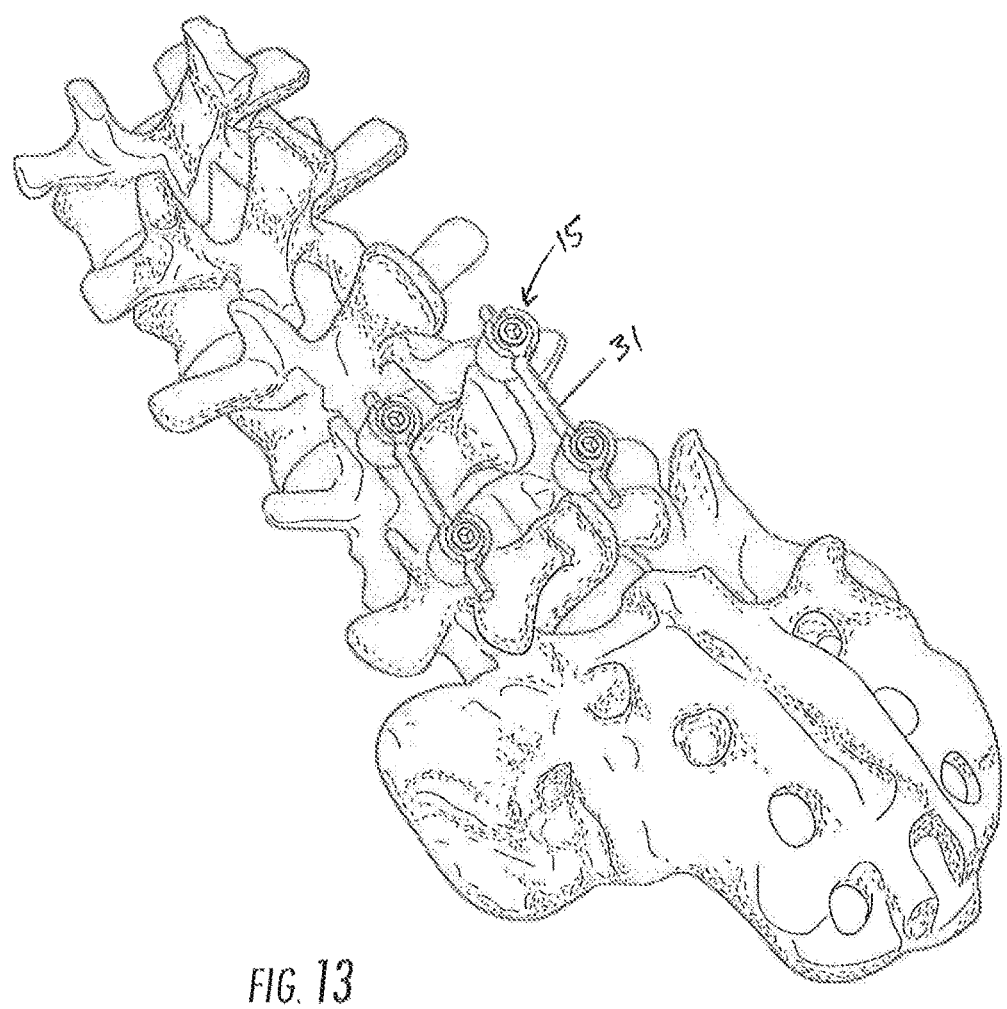
FIG. 13 illustrates a further embodiment of intervertebral stabilization structures positioned along the posterior surface of the spine.
Figure 14:
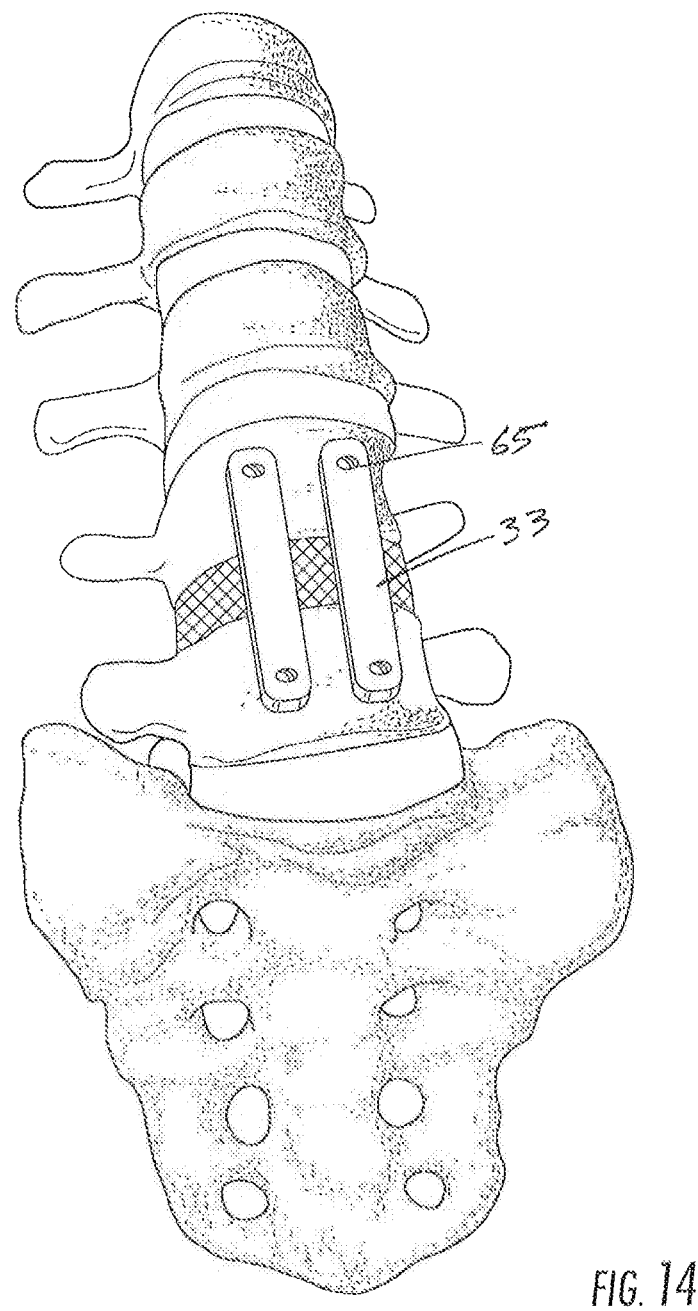
FIG. 14 illustrates a further embodiment of intervertebral stabilization structures positioned along the anterior surface of the spine.

FIG. 13 illustrates an embodiment where the screws 5 (hidden from view but similar to those of FIG. 8i) include polyaxial connector assemblies 15 securing rods 31 between adjacent vertebrae on the posterior side of the spine. FIG. 14 shows the anterior view of this embodiment where plates 33 extend between the vertebrae and cap pieces 65 secure the plates to the screws 5. The cap pieces 65 in FIG. 13 would differ from those seen in FIG. 8i in that the former would lack the external threads 68 shown in FIG. 8i. Although not explicitly seen in FIG. 14, the plates 33 could have an angled cross-section such as seen in FIG. 6d. The position of the angled surfaces of the plates would be such that the plates exhibit a slight rotation in the medial direction to accommodate the posterior-lateral to anterior medial orientation of the screws 5 (i.e., such as seen in FIG. 4).

Figure 11:
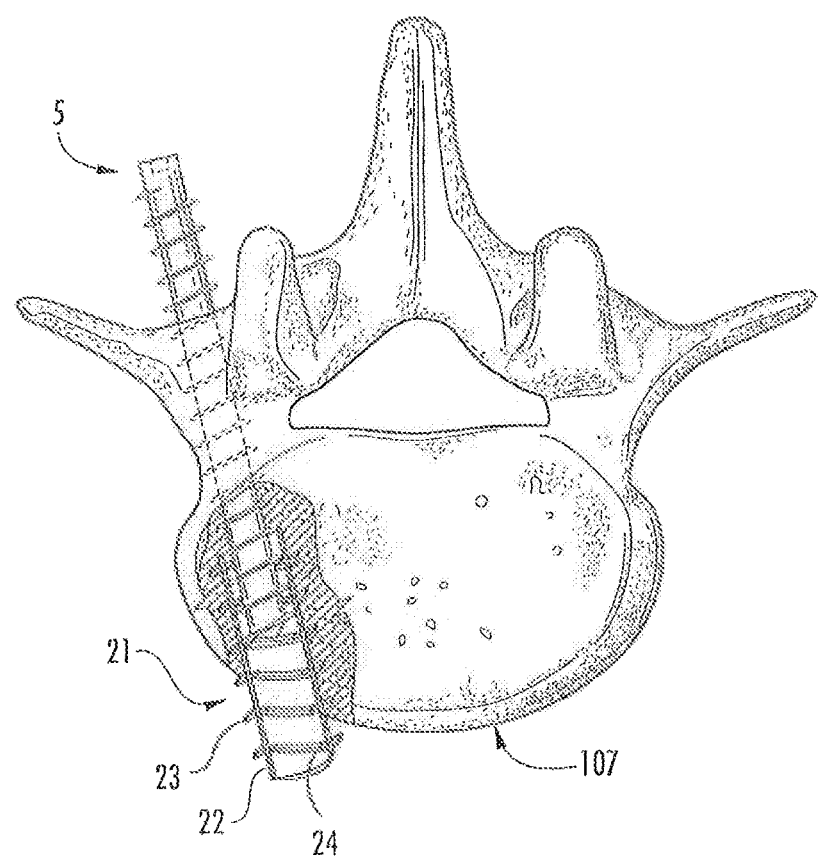
FIG. 11 illustrates another embodiment of hardware for securing the pedicle screw in the vertebral body.

A further embodiment shown in FIG. 11 suggests another fastener device to engage screw 5. In this embodiment, the cylindrical fastener 21 includes a hollow cylindrical body 22 having both external threads 23 and internal threads 24. A bore would be drilled into anterior vertebra surface 107 to accommodate cylindrical body 22. As suggested in the cut-away portion of FIG. 11 showing the living bone tissue, the external threads 23 would grip the bone tissue to secure fastener 21 within the vertebral body. Although not seen in FIG. 11, the end of cylindrical body 22 extending from the vertebral body could include any type of surface allowing a tool to apply torque to cylindrical body 22. Screw 5 advancing through the pedicle and into the vertebral body would then be able to engage the internal threads 24 to be secured in place. Preferably, cylindrical fastener 21 will be positioned such that screw 5 may advance a good distance into vertebral body 107 before engaging cylindrical fastener 21. An ISS could be attached to fastener 21 in any convention manner. For example, another screw (not illustrated) could pass through the ISS and engage the internal threads 24 of fastener 21.

There are many surgical procedures where the above described method may be employed. Nonlimiting examples could include: anterior or posterior fusions (particularly lumbar fusions) using a pair of ISSs on the anterior or posterior sides of the spine; these could include anterior lumbar interbody fusion (ALIF) procedures where stabilization structures are positioned only on the anterior side of the spine; or "360°" ALIF procedures where two parallel ISSs are positioned on the anterior side and two parallel ISSs are positioned on the posterior side of the spine. Other example procedures include stabilizations of lumbar burst fractures or lumbar corpectomies using anterior and posterior ISSs to create 360° stabilization system as suggested in FIGS. 9 and 10; for example a an L4 corpectomy (i.e., connecting the L3 to the L5 vertebra) or an L5 corpectomy (i.e., connecting the L4 to the S1 vertebra). FIG. 10 also illustrates the positioning of a interbody graft 55 (e.g., allograft bone or a hollow titanium cage) between vertebral bodies 101a and 101b which could be employed in many stabilization techniques.

Figure 15:
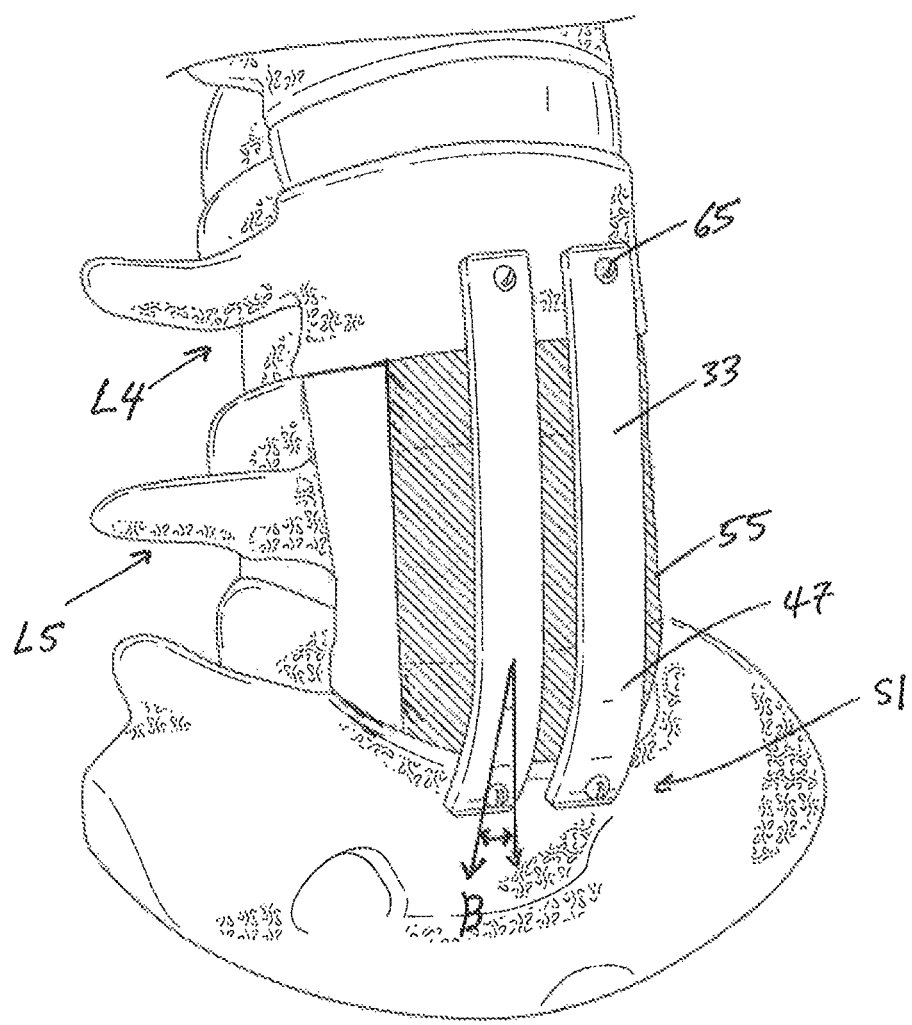
FIG. 15 illustrates an alternative embodiment of intervertebral stabilization structures positioned along the anterior surface of the spine where a portion of the L5 vertebra has been removed.

FIG. 15 illustrates one example of an L5 corpectomy utilizing an ISS formed with modified plates 33. A portion of the L5 vertebra and the corresponding discs above and below the L5 vertebra have been removed and replaced with an interbody graft 55. FIG. 15 shows plates 33 secured to the L4 vertebra with cap pieces 65. Although hidden from view in FIG. 15, this embodiment will connect to a pedicle screw placed at a lateral to medial, posterior to anterior orientation such as seen in FIG. 4. The opposing ends of plates 33 are secured to the S1 vertebra likewise using cap pieces 65. However, the opposing ends of plates 33 will have a curved portion 47 corresponding approximately to the section of plates 33 which extend from the point previously the bottom of the L5 vertebra to the plates' ends. As seen in FIG. 15, the curvature is in the anterior to posterior direction with respect to the long axis of the plate bodies. In one embodiment, the angle β of this curved portion 47 with respect to the long axis of plate 33, as measure from the beginning of the curve to the lower end of the plate 33, is between about 5° and 80° (or any sub-range there between, e.g., about 10° and 40°). In the FIG. 15 embodiment, the length of the curved portion 47 is about 25% to about 33% of the entire length of plate 33.

Figure 16:
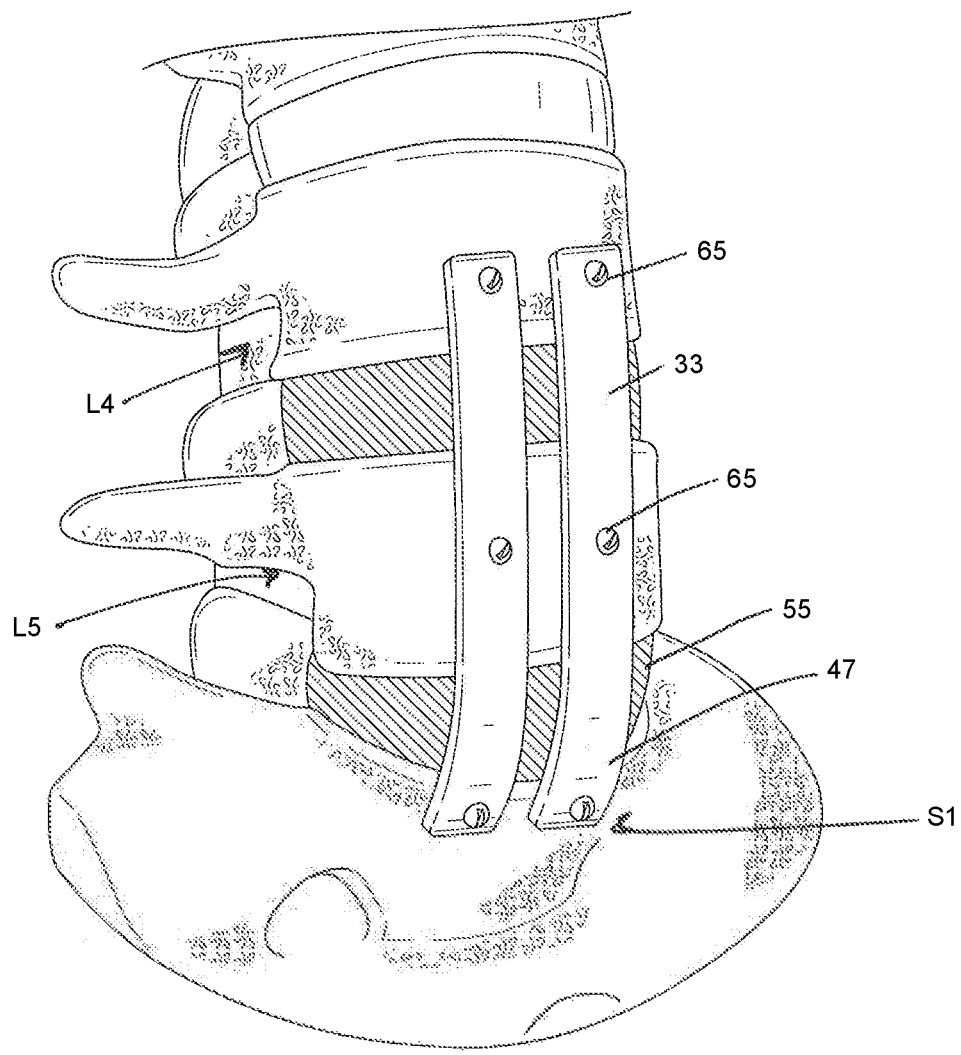
FIG. 16 illustrates the FIG. 15 intervertebral stabilization structures fixed to the L5 vertebra.
Figure 17:
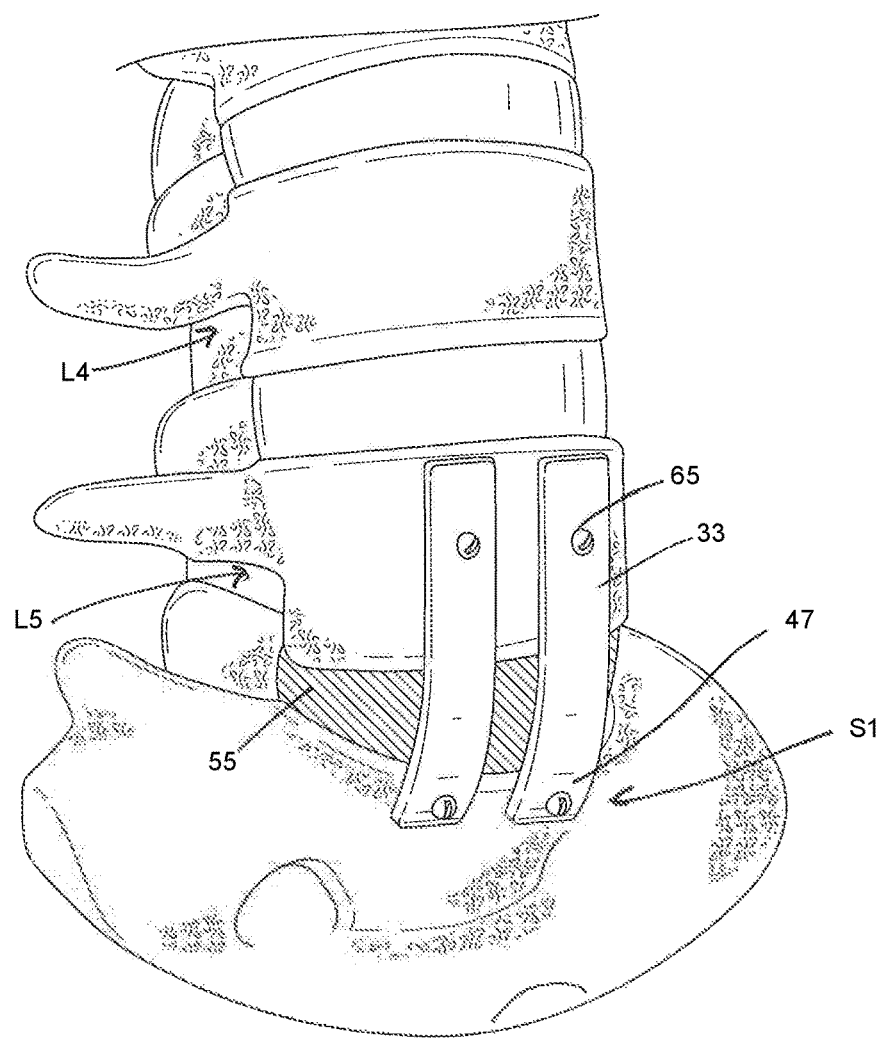
FIG. 17 illustrates the FIG. 15 intervertebral stabilization structures limited to the L5-S1 vertebrae.

FIG. 16 illustrates the same plates 33 utilized in a disckectomy procedure (e.g., where the L5 vertebra remains and only the discs above and below have been replaced with grafts 55). Here the plates have been affixed not only to the L4 and S1 vertebra, but also the L5 vertebra. Finally, FIG. 17 illustrates a shortened version of plates 33 which extend only between the L5 and S1 vertebrae. In the FIG. 17 embodiment, the length of the curved portion 47 is about 33% to about 50% of the entire length of plate 33.

Although the method embodiments described above contemplated turning the patient from the prone position to the supine position, other embodiments could potentially perform the posterior and anterior access to the spine while the patient in the lateral position (i.e., on the patient's side), thereby eliminating the need to turn the patient during the procedure. Nor do all method steps need to be practiced in the order discussed above, but in particular situations, the steps could be carried out in a different order.

Figure 12:
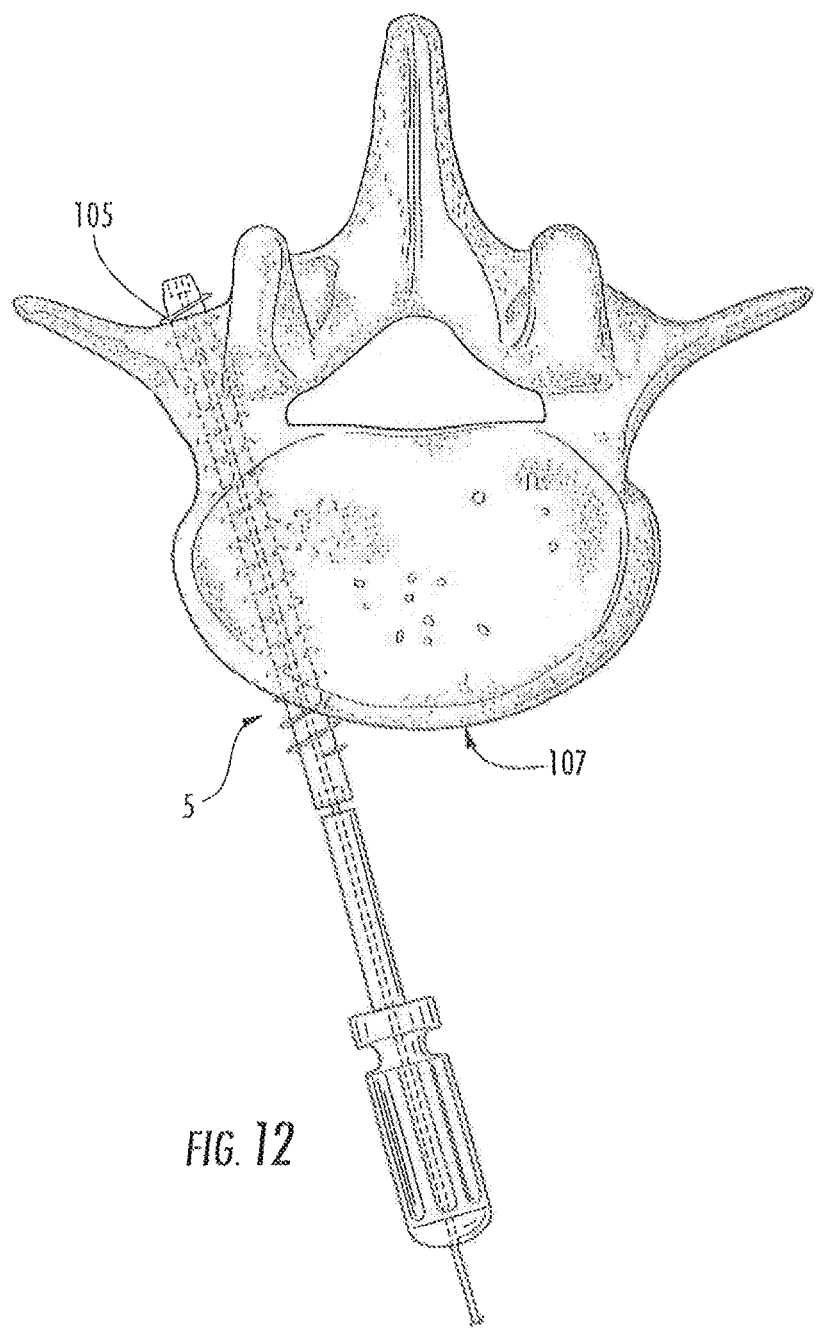
FIG. 12 illustrates an alternative method with the pedicle screw being advanced through the vertebral body from the anterior side to the posterior side.

A still further variation in the invention is seen in FIG. 12. FIG. 12 illustrates an alternative method where the screw 5 is inserted from the anterior side into the vertebral body and is advanced along a trajectory which has the screw traversing the pedicle and exiting posteriorly from the pedicle thru the bony elements at point 105. This embodiment of screw 5 is similar to that seen in FIGS. 8e and 8h in that it lacks a spherical head in order to accept a lower profile ISS and securing nut-type fastener (as opposed to a spherical head used with polyaxial connector devices). In this embodiment, each end of the screw may project 10-30 mm (and more preferably 10-20 mm) outside the bone tissue, which suggests the screw should have a length of between 50 and 120 mm, and more preferably between 70 and 100 mm. The trajectory of the screw could be obtained using any of the surgical navigation techniques described above. The method of FIG. 12 has the advantage of allowing the distal end of screw 5 to actually exit posterior pedicle point 105 (thereby eliminating the danger of striking blood vessels) and eliminating the step of drilling into bone tissue to locate the tip of screw 5.

While the above embodiments have been described in terms of methods of spinal stabilization, the present invention also includes the various apparatuses described in carrying out the methods. For example, a further embodiment of the invention includes a pedicle screw having a cannulated shaft with external threads and an enlarged head segment on one end of the shaft. A first drive socket is positioned in the enlarged head segment and a second drive socket on a shaft end opposite the first drive socket. Another embodiment includes a spinal stabilization system which include a pedicle screw and an intervertebral stabilization structure. The pedicle screw has a shaft with external threads and a head segment on one end of the shaft, a first drive socket positioned in the head segment, and a second drive socket on a shaft end opposite the first drive socket. The intervertebral stabilization structure has an elongated body with rotating ring segments attached to each end of the elongated body.

A further embodiment of a spinal stabilization system will include both a posterior stabilization bar (or typically a pair of posterior stabilization bars) and an anterior stabilization bar (typically a pair of anterior stabilization bars). The system will include at least two pedicle screws for each set of posterior/anterior stabilization bars. Where the posterior stabilization bar is a rod, the pedicle screws may have polyaxial connectors on the screw ends connecting to the posterior stabilization bar (e.g., as shown in FIGS. 8g and 13). If the anterior stabilization bar is a plate with a screw aperture (e.g., FIG. 6a), or a rod with screw apertures (e.g., FIG. 5), or a plate with swiveling ring connectors (FIG. 7b), then an anterior connector such as cap piece 65 (FIG. 8i) will secure the anterior bar to the pedicle screw. Alternatively, the anterior connector could be a second polyaxial head (FIG. 8j) in situations where the anterior stabilization bar is also a rod. Another alternative method for spine stabilization comprises the steps of: (a) accessing the anterior side of the spine, (b) advancing a screw into the anterior side of the spine and toward the posterior pedicle surface of a first vertebra until the screw exits the posterior pedicle surface, (c) repeating steps (a) and (b) at a second vertebra, (d) wherein the screw comprises: i) a first drive socket; (ii) a threaded shaft extending from the first drive socket; (iii) a second drive socket on a shaft end opposite the first drive socket, and (iv) a length such that 10-30 mm of the screw extends from both the pedicle surface and the anterior surface; and (e) wherein intervertebral stabilization structures are fixed between the first and second vertebra by attaching to the screws on the posterior side of the spine and the anterior side of the spine.

A still further embodiment is a spinal stabilization system comprising: (a) a pedicle screw comprising: (i) a shaft body with external threads and first and second shaft ends; (ii) a first drive socket positioned on the first shaft end; (iii) a second drive socket on the second shaft end; (iv) wherein the shaft has a length of between about 60 mm and about 120 mm; and (b) an intervertebral stabilization structure comprising an elongated body with an aperture for sliding over either the first or second shaft end. Alternatively in this embodiment, the shaft end opposite the first drive socket may a lesser diameter than the shaft end at the head segment. While the invention has been described in terms of certain specific embodiments, those skilled in the art will understand that there are many obvious variations and modifications of the described embodiments. All such variations and modifications are intended to come within the scope of the following claims.

The invention claimed is:

1. A pedicle screw comprising a shaft with first and second ends, wherein (i) the first and second ends include an internal drive socket and a first set of external threads; (ii) the shaft includes a mid-region having a second set of external threads, the second set of threads being courser than the first set of threads on the first and second ends; and (iii) the internal sockets include a depth which does not extend to the mid-region having the courser external threads.

2. The pedicle screw of claim 1, where a polyaxial connector assembly is threadedly attached to the first end of the shaft.

3. The pedicle screw of claim 2, where the polyaxial connector assembly includes a ball portion which is threaded onto the first end of the shaft.

4. The pedicle screw of claim 3, further comprising a cap piece configured to be threaded onto the shaft second end, the cap piece including a substantially flat head portion with a drive socket formed in the head portion.

5. The pedicle screw of claim 4, where the cap piece has a shank portion including a set of internal threads configured to engage the shaft second end.

6. The pedicle screw of claim 5, where the shank portion includes a set of external threads, courser than the internal threads and configured to engage bone.

7. The pedicle screw of claim 1, where the shaft first end has a first outer diameter, the shaft second end has a second, smaller outer diameter, and the shaft has a substantially constant taper between the first and second ends.

8. The pedicle screw of claim 1, where the shaft is cannulated.

9. The pedicle screw of claim 1, where the shaft has a length of between about 30 mm and about 70 mm.

10. A pedicle screw comprising a shaft with first and second ends, wherein (i) the first and second ends have an internal drive socket; (ii) at least the second end has a first set of external threads; and (iii) the shaft includes a mid-region having a second set of external threads, the second set of threads being courser than the first set of threads; (iv) the internal sockets include a depth which does not extend to the mid-region having the courser external threads; and (v) the shaft has a length of between about 30 mm and about 70 mm.

11. The pedicle screw of claim 10, wherein (i) the first end of the shaft includes a second set of external threads, and (ii) a polyaxial connector assembly is threadedly attached to the first end.

12. The pedicle screw of claim 10, where the first end of the shaft has a ball connector formed integrally thereon.

13. The pedicle screw of claim 12, wherein the shaft is cannulated.

14. The pedicle screw of any one of claim 11, 12, or 13, wherein the polyaxial connector or the ball connector extends beyond the between about 30 mm and about 70 mm length of the shaft.

* * * * *